United States Patent [19]
Dertzbaugh

[11] Patent Number: 6,008,329
[45] Date of Patent: Dec. 28, 1999

[54] METHOD FOR PURIFYING CHOLERA TOXIN

[75] Inventor: Mark Dertzbaugh, Fairfield, Pa.

[73] Assignee: The United States of America as represented by the Secretary of the Army, Washington, D.C.

[21] Appl. No.: 09/035,910

[22] Filed: Mar. 6, 1998

[51] Int. Cl.$^6$ .............................. C07K 17/14; C07K 14/28
[52] U.S. Cl. .............................................. 530/417; 530/825
[58] Field of Search ..................................... 530/417, 825

[56] References Cited

U.S. PATENT DOCUMENTS

| | | | |
|---|---|---|---|
| 5,563,046 | 10/1996 | Mascarenhas et al. | 435/69.52 |
| 5,674,677 | 10/1997 | Peterson | 435/5 |

OTHER PUBLICATIONS

Buckley et al., "The role of calcium influx in cellular proliferation induced by interaction of endogenous ganglioside GM1 with the B subunit of cholera toxin", Biochimica et Biophusica Acta, 1995, 1256, pp. 275–283.

Dertzbaugh et al., "Cholera toxin B–subunit gene fusion: structural and functional analysis of the chimeric protein", Infection and Immunity, 1990, vol. 58, No. 1, pp. 70–79.

Kazemi et al., "Mapping epitopic regions of cholera toxin B–subunit protein", Molecular Immunology, 1991, vol. 28, No. 8, pp. 865–876.

Clements et al., "Immunological cross–reactivity between a heat–labile enterotoxin(s) of *E.coli* and subunits of Vibrio cholerae enterotoxin", Infection and IMmunity, 1978, vol. 21, No. 3, pp. 1036–1039.

*Primary Examiner*—Sandra E. Saucier
*Assistant Examiner*—Vera Afremova
*Attorney, Agent, or Firm*—Charles H. Harris; John Francis Moran

[57] ABSTRACT

The invention relates to a method of purifying cholera toxin using a matrix with at least one ion chosen from among matrix with $Ni^{+2}$, $Co^{+2}$, $Cd^2$ or $Zn^{+2}$ immobilized thereon. It is possible thereby to selectively elute the B subunit for cholera toxin from the matrix.

5 Claims, No Drawings

METHOD FOR PURIFYING CHOLERA TOXIN

FIELD OF THE INVENTION

This invention relates to affinity matrix with the $Ni^{+2}$, $Co^{+2}$, $Cd^{+2}$ or $Zn^{+2}$ ion immobilized thereon which binds cholera toxin. The matrix may be used in purification of cholera toxin and for performing separation of the B subunit from the A subunit when the linkage between the units has been broken.

BACKGROUND OF THE INVENTION

Cholera toxin (CT) is composed of two subunits: a toxigenic A subunit (CTA), and a binding B subunit (CTB). The latter mediates binding of CTA to the surface of eukaryotic cells via its interaction with the monosialoganglioside GM1. The type I heat-labile enterotoxin of *Escherichia coli* (LT) is closely related to CT. It has an identical subunit structure and function, and shares 80% amino acid homology with CT. Although LT is very similar to CT in structure and function, it binds to a broader array of ligands than CT, including glycolipids and glycoproteins.

The 3-D crystal structure has been determined for both CT and LT. In addition, the crystal structure of CTB complexed with the GM1-pentasaccharide has also been determined. The crystal structure of this complex has revealed all interactions between the GM1 head group and the receptor binding site of CTB without any indication of the presence of a divalent ion binding site. Also, no biochemical evidence indicating that cations mediate ganglioside binding has previously been reported. However, some of the receptors for these enterotoxins have only been recently identified. Thus, it is possible that there are additional receptors for CT and LT that are still unknown.

An affinity method has been described for CT previously which employs the GM1 oligosaccharide as the ligand (Tayot et al., (1981) *Eur. J. Biochem.*, 113, 249–258.). However, this affinity matrix is not commercially available and the protein must be eluted from the column under extremely acidic conditions. Another method has been described based on the affinity of CT and LT for D-galactose (Uesaka et al., (1994) *Microb. Path.*, 16, 71–76). Like the Ni-NTA agarose, this column matrix is commercially available and elution is performed under mild conditions. The method described in this patent application provides yet another affinity purification method for CT and CTB.

SUMMARY OF THE INVENTION

It is the purpose of this invention to provide means for purifying cholera toxin using affinity matrix with the $Ni^{+2}$, $Co^{+2}$, $Cd^{+2}$ or $Zn^{+2}$ ion immobilized thereon to bind the toxin. It is also a purpose of this invention to provide a means of isolating the B subunit of cholera toxin when the linkage between the subunits has been broken. The toxins could be administered as vaccines. The invention provides compositions of matter comprising a matrix with at least one ion chosen from among the $Ni^{+2}$, $Co^{+2}$, $Cd^{+2}$ or $Zn^{+2}$ ions immobilized thereon bound to a site on the B unit of cholera toxin. The method of purifying cholera toxin comprises: 1. applying a composition containing the B subunit of cholera toxin to a matrix with $Ni^{+2}$, $Co^{+2}$, $Cd^{+2}$ or $Zn^{+2}$ immobilized thereon, 2. retaining the elute containing the B subunit of the cholera toxin on said matrix, 3. removing unbound material from the matrix of step 2, and 4. eluting the B subunit from the matrix.

DETAILED DESCRIPTION OF THE INVENTION

Cholera toxin (CT) was shown to bind to immobilized $Ni^{+2}$ ion. The affinity of CT for the complex required the presence of the $Ni^{+2}$ ion, since CT was unable to bind in its absence. Binding was mediated by the B-subunit (CTB) as both CT and CTB bound to the resin, but not the A-subunit (CTA). Binding was reversible in the presence of imidazole, and suggested that the affinity of CT for the $Ni^{+2}$ ion was mediated by His residues. The heat-labile enterotoxin of *Escherichia coli* (LT), which is closely related to CT, was unable to bind to the $Ni^{+2}$ ion. Comparison of amino acid sequences revealed the presence of three His residues in CT (positions 13, 57, and 94), but only one in LT (position 94). To confirm that the residues at positions 13 and 94 of CTB were responsible for the binding, they were changed to residues found in LTB. Changing His13>Arg completely abrogated the ability of CTB to bind to $Ni^{+2}$ ion. In contrast, mutation of His 94>Asn reduced, but did not abrogate, the ability of CTB to bind to $Ni^{+2}$ ion. Based on calculated bond distances, it is unlikely that His13 and His94 are part of the same complex. There appear to be two separate binding sites, with the principal site involving His13, and a much weaker site involving His94. This latter site can only participate in binding if the complex involving His13 has formed.

The methods of the invention were developed in the course of work related to the immunization against cholera. The toxins of the invention may be administered mucosally to provide protection from morbidity arising from exposure to cholera. The mechanism of binding and the amino acid residues that are critical for $Ni^{+2}$ binding to occur are disclosed herein.

Materials and Methods

Proteins and Reagents

Cholera toxin (CT), the A subunit (CTA), and biotinylated CTB were purchased from List Biological Laboratories (Campbell, Calif.) and were purified from *V. cholerae* Inaba strain 569B. Recombinant CTB was derived from the El Tor strain 62746, and was expressed and purified as previously described (Dertzbaugh and Elson, (1993b) *Infect. Immun.*, 61, 384–390). Purified type I human *E. coli* heat-labile enterotoxin (LT-h) was derived from strain Hc22/TP235 km and was purchased from Berna Products (Coral Gables, Fla.). Sepharose CL-6B, composed of highly cross-linked agarose, was purchased from Pharmacia (Piscataway, N.J.). Ni-NTA coupled to Sepharose CL-6B resin and Ni-NTA coated ELISA plates were purchased from Qiagen (Chatsworth, Calif.).

Mutagenesis of CTB

Plasmid pCVD002, encoding the CT genes of *Vibrio cholerae* El Tor strain 62746, was used as the template DNA for oligonucleotide-directed PCR mutagenesis of the CTB gene (Lockman and Kaper, (1983) *J. Biol.Chem.*, 258, 13722–13726). Oligonucleotides encoding the missense mutations His13>Arg13 (CAC>CGG) or His94>Asn94 (CAT>AAT) were used as mutagenic primers. Each mutagenic oligonucleotide was combined with a non-mutagenic oligonucleotide to form a pair of flanking primers to modify the PCR-amplified template DNA. A double mutant incorporating both the R13 and N94 codon changes was also constructed by employing both mutagenic oligonucleotides as flanking primers in the PCR. Amplification was performed using Vent polymerase (New England Biolabs, Beverly, Mass.). The reaction mixture was prepared according to the manufacturer's directions and then subjected to 25 cycles of the following temperature sequence:

94° C. for 1 min; 43° C. for 1 min; 72° C. for 1 min. The PCR-amplified product was directionally cloned into the expression vector pMTD107 as an EcoRI-BamHI fragment. Plasmid pMTD107 was derived from pET-8c (Studier et al., (1990) *Meth. Enzymol.*, 185, 60–89.) and includes a cassette encoding the ompA leader sequence (Ghrayeb et al., (1984) *EMBO J.*, 3, 2437–2442). In-frame insertion of a gene downstream of this sequence will result in expression of a fusion protein containing the OmpA leader peptide on its N-terminal end. Transformation of pMTD107 into the lysogenic *E. coli* strain HMS174(DE3) permits IPTG-inducible expression of protein from the T7 promoter (Studier et al., 1990). Induced lysates were screened for expression of CTB by a sandwich ELISA, using goat anti-CTB (Calbiochem, LaJolla, Calif.) as the capture reagent and rabbit anti-CT (Sigma) as the primary antibody.

Expression and Harvest of CTB Mutants

*E. coli* strains expressing mutant CTB were grown and induced as described previously (Dertzbaugh and Elson, 1993b *Infect. Immun.*, 61, 384–390). A whole cell lysate was prepared by suspension of the cell pellet in 1/10 culture volume of lysis buffer (20% sucrose, 50 mM Tris, 50 mM EDTA, pH 8.0) containing 1 mg/ml lysozyme. The suspension was incubated for 30 min at 37° C. and then diluted to one culture volume with distilled water prior to being subjected to 2 cycles of rapid freeze-thaw. The lysate was clarified by centrifugation at 20,000×g for 20 min at 4° C. Mutant CTB protein was isolated from the lysate by fractional 20–60% $NH_4SO_4$ precipitation. This material was used for all of the resin binding studies. For use in the competitive assays, the protein preparations were extensively purified. Briefly, $NH_4SO_4$ precipitates containing mutant CTB were dialyzed in imidazole buffer (20 mM imidazole, 20 mM NaCl, pH 7.0) and then eluted from a MonoQ HR10/30 anion exchange column (Pharmacia, Piscataway, N.J.) using a 0–250 mM NaCl gradient. Fractions containing protein were pooled and concentrated by ultrafiltration using an Amicon YM3 membrane (Amicon, Beverly, Mass.). The concentrated protein was eluted from a Superdex 75 HR26/60 gel filtration column (Pharmacia) equilibrated in TEAN buffer (50 mM Tris, 1 mM EDTA, 200 mM NaCl, 3 mM $NaN_3$, pH 7.5). Fractions containing protein were pooled and adjusted to a final concentration of 1.0 mg/ml based on their absorbance at 280 nm. The purity of the CTB proteins was determined by coomassie blue staining of samples separated by SDS-polyacrylamide gel electrophoresis to be >90%.

Reduction and Alkylation of CTB

Purified recombinant CTB was dialyzed against 50 mM Tris, pH 8.0 and then degassed in nitrogen for 20 min. Sodium dodecyl sulfate (SDS) and 2-mercaptoethanol (2-ME) were added to final concentrations of 1% and 0.2 M, respectively, and the solution was incubated at 37° C. for 4 h. Reduced sulfhydryl groups on CtxB were alkylated by the addition of a 10-fold molar excess of iodoacetic acid (IAA). Alkylation proceeded for 1 h at 25° C. SDS was removed from the suspension by passing it through a column containing Extract-D-Gel resin (Pierce) equilibrated in 50 mM Tris, pH 8.0. The suspension was dialyzed exhaustively against TBS, pH 7.5 and then stored at 4° C. before use.

Resin Binding Studies

Protein samples precipitated with $NH_4SO_4$ were extensively dialyzed against several changes of Tris-buffered saline (TBS: 20 mM Tris, 100 mM NaCl, pH 8.0) prior to addition to the resin. To prepare NTA-Sepharose devoid of the $Ni^{+2}$ ion, the Ni-NTA Sepharose was washed with several changes of EDTA buffer (100 mM EDTA, 20 mM Tris, 100 mM NaCl, pH 8.0). The Ni-NTA Sepharose, NTA-Sepharose, and Sepharose CL-6B resins were each equilibrated with wash buffer prior to addition of the protein samples. The samples were gently mixed for 15 min with 400 μl of a 50% slurry of resin. Each suspension was centrifuged briefly to pellet the resin, and the supernate was analyzed for the presence of unbound protein. The resin was washed six times with a 1 ml volume of TBS, and bound protein was eluted from the resin by step-wise batch elution with increasing concentrations of imidazole in TBS. The suspension was gently mixed for 5 min with each concentration of imidazole to facilitate elution. As a final step, the resin was washed with 1 ml of EDTA buffer in order to remove any tightly bound protein. Samples were separated by SDS-polyacrylamide gel electrophoresis (SDS-PAGE) and stained with coomassie blue to visualize CTB.

Competitive Ni-NTA ELISA

Biotinylated CTB, diluted to a concentration of 500 ng/ml in TBS pH 8.0 containing 10 mM $NiSO_4$ (TBSN), was added to each well of a pre-blocked uncoated polyvinyl microtiter plate. As a negative control, one set of wells did not receive any biotinylated CTB. Each competitor was initially diluted to a concentration of 1.72 μM in TBSN and then serially diluted 2-fold. Each dilution was performed in quadruplicate. As a positive control, one set of wells did not receive any competitor. The contents of each well were transferred to identical wells of a 96-well plate pre-coated with Ni-NTA (Qiagen), and the plate was incubated overnight at 4° C. Phosphatase-labeled streptavidin (KPL) diluted in TBS +1% bovine serum albumin (BSA; Sigma) was used as the secondary reagent. The $A_{405}$ was determined for each well using p-nitrophenyl phosphate as the substrate.

Crystal Structure Analysis

Bond distances between atoms were calculated based on the coordinates deposited in the Brookhaven Protein Data Bank (PDB Id: 1FGH) (Zhang et al., (1995b) *J. Mol. Biol.*, 251, 550–562). The program RasMol (version 2.6 beta) was used to identify amino acid residues and to calculate bond distances (Sayle and Milner-White, (1995) *Trends Biochem. Sci.*, 20, 374).

Results

Subunit Affinity and Binding Specificity of CTB

Purified samples of cholera toxin (CT), the A subunit (CTA), and the B subunit (CTB) were evaluated for their ability to bind to the Ni-NTA agarose resin. CT and CTB were both able to bind to the Ni-NTA resin with high affinity. Trace amounts of CTA were detected in the imidazole wash, but at very low levels, compared to the pre-resin sample. In order to determine what component of the gel matrix mediated binding, purified samples of CTB were mixed with the following resins: Sepharose CL-6B, NTA-Sepharose, and Ni-NTA Sepharose. By using a combination of these resins, it was possible to determine whether CTB was binding directly to the Sepharose-based bead, the NTA spacer arm, or the $Ni^{+2}$ ion. It was found that the ability of CTB to bind to the resin is clearly dependent on the presence of the $Ni^{+2}$ ion. CTB did not bind to the Sepharose CL-6B or to the NTA spacer arm.

Inability of LT or Denatured CTB to Bind to the Resin

A purified sample of *E. coli* heat-labile enterotoxin (LT) was examined for its ability to bind to the Ni-NTA resin. The affinity of LT for the Ni-NTA resin was very poor compared to CT. In order to determine whether there was a structural requirement for CTB to bind to the resin, a sample of the protein was reduced and alkylated to eliminate disulfide bond formation. Reduction has been shown previously to eliminate the ability of CTB to bind to GM1 ganglioside. An ELISA based on the ability of CTB to bind to GM1 confirmed that the reduced form of CTB retained only 0.6% of its original binding activity. The reduced form of CTB was unable to bind to the resin, demonstrating that there is a conformational requirement for CTB to bind to the $Ni^{+2}$ ion.

Affinity of CTB Mutants for $Ni^{+2}$ Ion

The ability of CTB to be eluted from the Ni-NTA agarose by imidazole suggested that His residues may be involved. To test this hypothesis, PCR-mutagenized versions of the CTB gene were constructed as follows: His13>Arg (R13), His94>Asn (N94), and a double mutant consisting of R13 and N94. The modified genes were inserted into the plasmid pMTD107, fused to the OmpA leader peptide, and expressed in E. coli strain HMS174(DE3) under control of the IPTG-inducible T7 promoter. The proteins expressed were extensively purified prior to use in the binding studies. Each mutant was evaluated for its ability to bind to Ni-NTA using a solid-phase competitive ELISA. Equimolar amounts of each protein were competed against a fixed amount of biotinylated CTB for binding to Ni-NTA coated plates. LT was unable to compete with CT and CTB for binding to $Ni^{+2}$ ion. Likewise, the R13 mutant was unable to compete. Interestingly, the R94 mutant was still able to compete with biotinylated CTB for binding, but at reduced levels. The R13-N94 double mutant was identical to the R13 mutant in its ability to compete for binding to $Ni^{+2}$ ion.

It is known that for most proteins to bind tightly to the Ni-NTA Sepharose, there must be a cluster of His residues that will form a coordination complex with the $Ni^{+2}$ ion. The greater the number of His residues clustered together, the greater the affinity of the protein for the Ni-NTA agarose. Amino acids such as Lys, Arg, and Trp may also bind to the $Ni^{+2}$ ion, but not with the affinity associated with His. The ability to elute CTB from the Ni-NTA resin using imidazole suggested that the binding was being mediated by His residues. The trace amounts of CTA that were observed in the eluate may have been due to incomplete removal of unbound protein, rather than any specific interaction of the protein with the resin. This was confirmed using a competitive Ni-NTA ELISA, which showed that CTA was unable to compete for binding to the $Ni^{+2}$ ion.

Despite its significant level of amino acid identity with CT, type I LT-h was unable to bind to $Ni^{+2}$ ion. Comparison of the amino acid sequence of each protein revealed that the El Tor strain of CTB used in this study encodes His residues at positions 13, 57, and 94. The porcine strain of LTB (LTB-p) encodes only one His residue, located at position 57. For this reason, the His at position 57 was not considered to play a critical role in the ability of CTB to bind to $Ni^{+2}$ ion. We concluded that the other two His residues in CTB, located at positions 13 and 94, may be responsible for the binding. To prove this, these residues were substituted for the amino acids that are encoded by LTB-p. Three mutants were constructed: His13>Arg (R13), His 94>Asn (N94), and a R13-N94 double mutant. These mutants were compared to CTB and LTB for their ability to bind to $Ni^{+2}$ ion. The R13 substitution completely abolished the ability of CTB to bind to $Ni^{+2}$ ion, while the N94 substitution resulted in a partial loss of binding activity. Thus, the affinity of CTB for $Ni^{+2}$ ion is due primarily to the His residue located at position 13.

The reason why these residues are involved in binding to $Ni^{+2}$ ion is not clear, but it appears that their spatial arrangement is critical for this to occur. Reduction of the intramolecular disulfide bridge within each monomer has been shown previously to dramatically affect the structure and ganglioside binding function of CTB. A similar effect was observed for $Ni^{+2}$ ion binding in this paper, supporting our hypothesis that CTB must be in the proper conformation to interact with the $Ni^{+2}$ ion.

Although the His residues in CTB are not located contiguous to each other within the linear protein sequence, they are located in the general proximity of the receptor binding cleft of each monomer. Without relying on any theory of mechanism for patentability, it should be appropriate to postulate that these His residues may be clustered sufficiently close to one another spatially to participate in the binding of CTB to $Ni^{+2}$ ion. To confirm this, the interatomic distance between N atoms was determined for each His residue based on the crystal structure data of CTB. This information was compared to the bond distances reported for the crystal structure of bis(histidino)nickel(II) monohydrate. Based on this information, none of the His residues are sufficiently close to each other to interact with $Ni^{+2}$ ion. Potential bond distances between His residues located on adjacent monomers were also examined, and were too distant to form a complex with $Ni^{+2}$ ion as well. Other nearby amino acids that could potentially participate in forming a complex with $Ni^{+2}$, such as Lys, Arg, and Trp, were also evaluated for their ability to interact with the His residues. Lys91 may be sufficiently close to His94 to form a complex, but none of these other residues appear close enough to form a complex with His13. Clearly, His13 is essential for binding. One possible explanation may be that His13 on one oligomer may form a complex with His13 located on another oligomer. His13 protrudes out from the surface of CTB, and could readily interact with free imidazole groups located close to it.

In view of the above, it is proposed that there are two separate binding sites for CTB. His13 is affiliated with one site and requires the participation of a His13 located on a different oligomer. This site is essential for binding, since changes made in His13 completely abrogated binding. In theory, there may be as many as five binding sites per oligomer. His94 is affiliated with the other site, and either requires the participation of Lys91 located on the same monomer or another residue, such as His94, located on a different CTB oligomer. Of the two possibilities, the latter appears more likely. No $Ni^{+2}$ binding was observed using the R13 mutant, even though the His at position 94 was still intact. Furthermore, only a partial loss of binding activity was observed using the N94 mutant. Formation of the primary complex requires participation of His13, which anchors the oligomers together tight enough to permit a secondary complex to form involving His94. This secondary complex is too weak to form on its own and is dependent on formation of the primary complex. Both of these binding sites would be dependent on the conformation of CTB, which is also consistent with the results of our denaturation study.

In addition to their difference in $Ni^{+2}$ binding, CT and LT are also different in the types of glycoconjugate receptors they recognize. There are only a few amino acid residues that differ between CTB and the various isolates of LTB, but the residues at positions 13 and 94 are two of them. These two positions have been postulated to be responsible for some of the differences in glycoconjugate binding specificities observed between CT and LT, but their precise role has not been determined experimentally.

It has not been possible to ascribe any specific biological function to the ability of CT to bind to $Ni^{+2}$ ion. The crystal structure of CTB complexed with the GM1-pentasaccharide has been elucidated, and indicates that receptor binding is not dependent on the presence of any particular cofactor.

Lanthanide binding sites have been identified at the A-B interface of LT, which suggests that LT may also bind $Ca^{+2}$ ion. This indirectly suggests that LT may act as a $Ca^{+2}$ ionophore. The B subunit of CT has previously been shown to possess pharmacological activity and to inhibit mitogen-induced T cell proliferation in vitro. Thus, it is possible that the ability of CTB to bind to $Ni^{+2}$ may be associated with some biological function that is not currently understood.

While the examples presented herein identify $Ni^{+2}$ as an appropriate ion for use on columns to selectively bind cholera toxin, more particularly, the B unit on the cholera toxin, whether that unit is bond to the A unit or is separated from the toxin and/or bound to other moieties, it would also be appropriate to use columns having $Co^{+2}$, $Cd^{+2}$ or $Zn^{+2}$ bound thereto in the manner described herein. (Compared to polyhistidine-tagged proteins, CTB has a relatively low affinity for $Ni^{+2}$ ion. The protein was eluted from the resin at a concentration of 42 mM imidazole.)

What I claim is:

1. A composition of matter comprising a matrix with at least one ion chosen from among $Ni^{+2}$, $Co^{+2}$, $Cd^{+2}$, and $Zn^{+2}$ ions immobilized on said matrix, having a natural site on the B subunit of cholera toxin bound to said $Ni^{+2}$, $Co^{+2}$, $Cd^{+2}$, and/or $Zn^{+2}$ ion on said matrix.

2. The composition of claim 1 wherein the B subunit is not bound to the A subunit of the cholera toxin.

3. The composition of claim 1 wherein the B subunit is bound to the ganglioside GM1.

4. The composition of claim 1 wherein $Ni^2$ ion is immobilized on the matrix.

5. A method of purifying cholera toxin comprising the steps of:
   (a) applying a composition containing the B subunit of cholera toxin to a matrix with $Ni^{+2}$, $Co^{+2}$, $Cd^{+2}$, and/or $Zn^{+2}$ immobilized thereon,
   (b) retaining the composition containing the B subunit of the cholera toxin on said matrix for sufficient time to allow binding the subunit through the $Ni^{+2}$, $Co^{+2}$, $Cd^{+2}$, and/or $Zn^{+2}$ ligand to said matrix,
   (c) removing unbound material from the product of step (b), and
   (d) eluting the B subunit from the matrix.

* * * * *